United States Patent [19]

Novikov

[11] Patent Number: 4,743,849
[45] Date of Patent: May 10, 1988

[54] MAGNETIZING DEVICE FOR RECORDING FLAW FIELDS IN THE PROCESS OF MAGNETOGRAPHIC INSPECTION

[75] Inventor: Alexei E. Novikov, Minsk, U.S.S.R.

[73] Assignee: Belorusky Politekhnichesky Institute, Minsk, U.S.S.R.

[21] Appl. No.: 856,344

[22] Filed: Apr. 28, 1986

[51] Int. Cl.$^4$ .................. G01N 27/85; H01F 13/00
[52] U.S. Cl. ............................ 324/213; 280/208; 324/226; 324/228; 335/284
[58] Field of Search .............. 324/200, 213, 214–216, 324/226, 228, 262; 335/209, 219, 284; 180/10; 280/206–208

[56] References Cited

U.S. PATENT DOCUMENTS

| | | | |
|---|---|---|---|
| 3,062,560 | 11/1962 | Dunstan | 280/208 |
| 3,718,342 | 2/1973 | Freed | 280/208 |
| 4,447,778 | 5/1984 | Stumm | 324/262 X |

FOREIGN PATENT DOCUMENTS 315112 10/1971 U.S.S.R.

Primary Examiner—Gerard R. Strecker
Attorney, Agent, or Firm—Lilling & Greenspan

[57] ABSTRACT

A magnetizing device includes a two-pole electromagnet with four rollers mounted in pairs on the poles of the electromagnet and interacts with a respective guide. These guides are made as rings. The rollers are mounted on the poles by means of half-axles which are secured on each roller with a displacement in relation to the rotation axle of the roller.

7 Claims, 1 Drawing Sheet

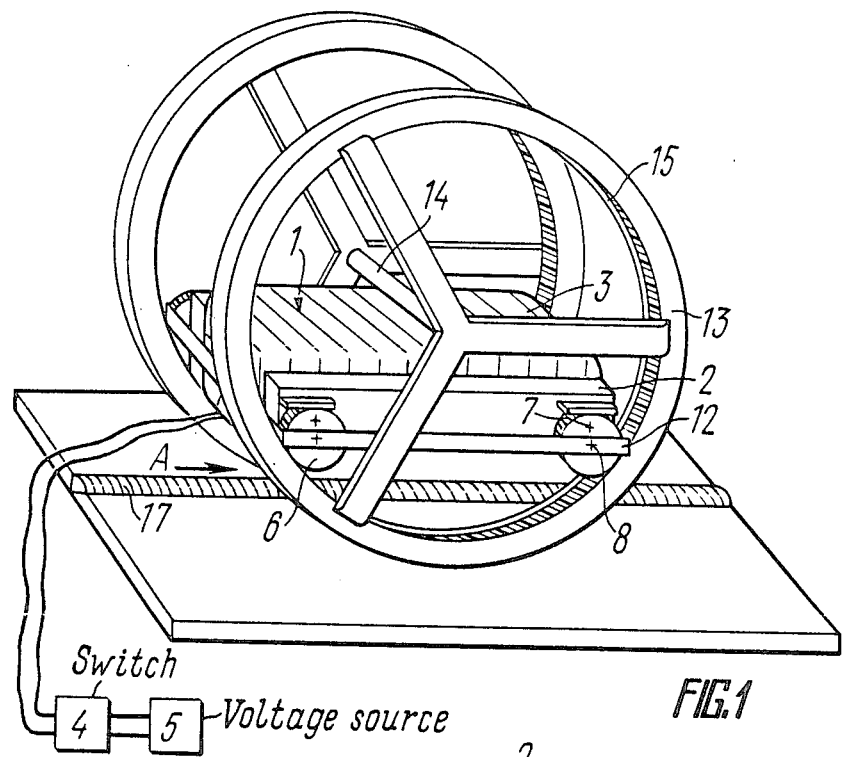
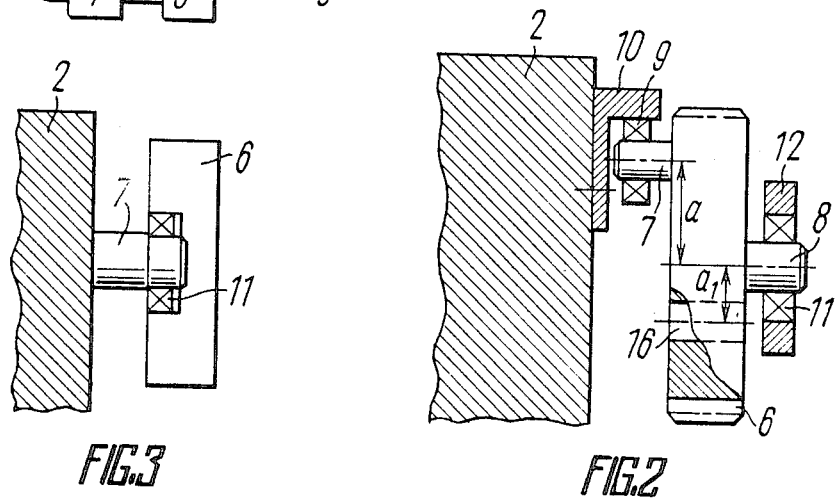

MAGNETIZING DEVICE FOR RECORDING FLAW FIELDS IN THE PROCESS OF MAGNETOGRAPHIC INSPECTION

BACKGROUND OF THE INVENTION

1. Field of the Invention

This invention relates to non-destructive test-instruments and, in particular, to magnetizing devices for magnetographic inspection, and is intended for magnetic recording of flaw fields during magnetographic inspection, for example, during weld inspection.

2. Description of the Prior Art

Known in the art is a device for magnetographic inspection, comprising a U-shaped two-pole electromagnet equipped with four rollers set in pairs on the poles of the electromagnet and two guides, each guide interacting with a respective pair of rollers. The guides are usually the surface of the inspected object, for example, during the inspection of welds it is the surface of the welded plates. As the magnetizing device is moved from one inspection zone to another it has to overcome numerous obstacles, such as irregularities of the surface, solidified metal splashes on the plate surface, misalignment of the plates, loose welding flux, etc. The precision of movement along inspection zones is also impaired. Moreover, when the device has to be transported over a corrugated or some other similar surface where the size of irregularities is comparable to the diameter of the rollers, the movement becomes extremely difficult if not impossible, considering the weight of the electromagnetic device (cf., for example, the USSR Inventor's Certificate No. 315,112, IPC G OI n 27/82 published in 1971).

SUMMARY OF THE INVENTION

One object of the invention is to provide easy and accurate movement of the magnetizing device from one inspection zone to another with only a minor effort applied thereto.

Another object of the invention is to provide stability of the magnetic contact of the electromagnet of the magnetizing device with the surface of the inspection zone.

One more object of the invention is to provide easy and convenient movement of the magnetizing device to a distance exactly equal to the inspection spacing.

The invention provides a magnetizing device for magnetographic inspection comprising a two-pole U-shaped electromagnet equipped with four rollers installed in pairs on the electromagnet poles and two guides, each guide interacting with a respective pair of rollers, in which, according to the invention, the guides are made as rings rigidly secured by connecting the central portions of the guides and interacting with the outer surfaces of the rollers by the inner surfaces thereof.

It is advisable that, in order to provide periodic contact of the electromagnet poles with the surface of the object being inspected, the rollers should be secured to the electromagnet poles by means of half-axles, one half-axle provided for each roller and displaced in relation to the rotation axle of this roller, supports of the rotation axles of the rollers being secured together by a rigid frame.

In order to adjust the height of the electromagnet during movement of the magnetizing device, it is advisable that the half-axles should be arranged on the rollers so that they can be displaced in relation to the axles of the rollers.

In order to prevent rollers slipping on the guides and to make the movement of the device more accurate, it is advisable that the inner surface of each roller and, respectively, the outer surface of each ring should be provided with gears in order to ensure engagement of the rollers and rings.

The magnetizing device for magnetographic inspection, made according to the invention, is convenient to use. It can be moved from one inspection zone to another by a minor effect, it can be moved over rough surfaces extremely accurately, the reliable contact of the electromagnet poles with the surface of the object under inspection being provided in the points of inspection spaced apart from one another at a distance equal to the inspection spacing.

BRIEF DESCRIPTION OF THE DRAWINGS

The invention will now be described in greater detail with reference to a specific embodiment thereof, taken in conjunction with the accompanying drawings, wherein:

FIG. 1 shows an isometric general view of a magnetizing device for magnetographic inspection, according to the invention;

FIG. 2 shows an enlarged sectional view, taken along the arrow A, of a place where the roller is connected with the electromagnet pole, according to the invention; and FIG. 3 shows the view of FIG. 2 where the displacement of the half-axle in relation to the roller rotation axle is equal to zero.

DETAILED DESCRIPTION OF THE INVENTION

A magnetizing device for magnetographic inspection, according to the invention, comprises (FIGS. 1 and 2) a U-shaped two-pole electromagnet 1 with a magnetic core 2 which consists of two vertical sections and a horizontal jumper interconnecting said sections on which jumper a current coil 3 is wound up, said coil being connected via a switch 4 to a voltage source 5. A pair of rollers 6 is installed on each pole of the electromagnet 1. The rollers 6 are connected to the poles of the electromagnet 1 by means of half-axles 7, one half-axle 7 for each roller 6 with a displacement "a" in relation to rotation axles 8 of the rollers 6, and roller bearings 9. The outer bearing races carry the electromagnet 1 whose four platforms 10 rest on said bearing races and are secured in pairs on each pole of the magnetic core 2. The axles 8 of the rollers 6 are placed in bearings 11 arranged in a frame 12 which supports all four rollers 6. Two ring-shaped guides 13 are rigidly secured together by a bar 14 connecting the central portions of the crosses fixed on the guides 13. The inner ring edges of the guides 13 are provided with flanges 15 which restrict the positions of the rollers 6 in the direction of the axles 8. Gear rings are provided on the outer surfaces of the rollers 6 and inner surfaces of the guides 13 to produce gear engagement. The half-axles 7 are mounted in the rollers 6 so that they can be displaced to a distance "a". To this end, at least one additional socket 16 is provided in the body of the roller 6, the axis of said socket 16 being displaced in relation to the axis of the axle 8 of the roller 6 to a distance $a_1 \neq a$.

FIG. 3 shows an embodiment of a device wherein the rollers 6 are installed without eccentricity when the axis of the half-axle 7 coincides with the rotation axis of the roller 6.

In some cases it is possible to use a magnetizing device equipped with rollers 6 and guides 13 without the gear rings.

The magnetizing device for magnetographic inspection operates as follows.

A magnetic flux is excited in the object of the magnetographic inspection. The force lines of the magnetic field in this case are located across the direction of movement of the magnetizing device along the inspection zone, for example, perpendicular to a weld. When a flaw, such as a crack or a cavity, is encountered in the path of the device, some magnetic force lines come to the surface of the object being inspected and produces a leakage field which is recorded on a magnetic tape in contact with the surface of the object being inspected.

For magnetographic inspection, the magnetizing device made according to the invention is placed on the surface of the object being inspected and the voltage source 5 (FIG. 1) is connected to the mains. The magnetizing device is then placed in an initial position above a weld 17 to be inspected and a portion of the weld 17 is magnetized by the electromagnet 1 after the switch 4 is turned on. After the magnetization operation, the windings 3 of the electromagnet 1 are deenergized, and the magnetizing device is moved to a next position to a distance equal to the inspection spacing. For this purpose the ring guides 13 are turned and the rollers 6 roll on the inner surfaces of the guides 13, the half-axles 7 (FIG. 2) secured to the rollers 6 acting via the bearings 9 on the platforms 10 rigidly attached to the magnetic core 2. As the half-axles 7 are mounted in the rollers 6 with a displacement "a", they describe, as the rollers 6 turn about their axles 8, circles with a radius equal to the displacement "a". The effort produced by the movement of the ring guides 13 along the weld 17 can be separated into two components—vertical and horizontal ones. Only the vertical component acts on the electromagnet 1 since it rests on the rollers 6 and the magnetic core 2 has its weight resting freely on the platforms 10 mounted on the bearings 9 fitted on the half-axles 7. The other, horizontal, component has no effect on the electromagnet 1 since the bearing 9 rolls on the supporting surface 10. In consequence, when the ring guides 13 are rolled over the surface of the inspected object, the electromagnet 1 moves forward and, simultaneously, moves at first upward and then downward until the contact with the inspected surface is established at a distance from the initial position, which is equal to the inspection spacing. This spacing depends on the diameter of the rollers 6 and can be easily adjusted by replacing the rollers 6 by rollers of another diameter.

When the magnetic core 2 of the electromagnet 1 is in contact with the surface of the inspected object, the winding 3 of the electromagnet 1 is energized. Then all the above mentioned operations are repeated. The leverage which is approximately equal to the diameter of the ring guides 13 makes the movement of even heavy magnetizing devices a very easy task. In addition, the use of the large-diameter guides 13 makes it possible to ignore the irregularities and pits on the surface of the inspected object when the magnetizing device is mounted from one location to another. Even when the zone to be inspected has some bulges or adjoining welds featuring various build-ups, the use of the magnetizing device according to the invention makes the movement easy by refitting the half-axles 7 into other sockets with great displacement in relation to the axles 8 of the rollers 6. The electromagnet 1 is lifted higher, since the eccentricity is larger, and the obstacle can be easily negotiated.

One more feature of this embodiment of the magnetizing device consists in that the gap between the poles of the electromagnet 1 and the inspected surface exists only when the magnetizing device is moved from one inspection location to another. On location the poles of the electromagnet 1 are in contact with the inspected surface, and the gap no longer exists.

The embodiment of the magnetizig device for magnetographic inspection shown in FIG. 3 provides for movement of the magnetizig device and the magnetization process with a permanently existing gap between the poles of the electromagnet 1 and the inspected surface. In this instance, the gap is determined by the place where the half-axles 7 are secured on the magnetic core 2 and is selected on the basis of obtaining optimal magnetization of the inspected object considering recording of flaws on the magnetic tape. This embodiment of the magnetizing device is cheaper and is especially practical when the objects of inspection are thin-walled easily magnetizable articles. In this case one can do without the gear mesh of the rollers 6 and the guides 13, since the size and weight of the electromagnet 1 are not large and the rollers 6 and guides 13 do not slip during movement.

The ring guides 13 can be made of both magnetic and non-magnetic material. This depends on the specific conditions of inspection and peculiarities of the object. When the magnetizing device has to be moved over an inclined surface, the guides 13 can be made of a magnetized highly coercive material. The magnetizing device can then be kept on a specific trajectory by the magnetic force lines closing through the object of the inspection.

What is claimed is:

1. A magnetizing device for recording flaw fields in the process of magnetographic inspection, comprising: a two-pole electromagnet having a working pole surface intended for contacting the surface of an object under inspection; four rollers rotatably mounted in pairs on each of the two poles of said electromagnet, each having a rotation axle defining a rotation axis, the rotation axes of said rollers all being arranged in one plane parallel to said working pole surface of said electromagnet; two ring-shaped guides each having a circular inner surface and each having a circular outer surface for rolling along the object under test, said ring-shaped guides being rigidly secured together in parallel relation to each other by a bar for simultaneous rotation of said ring-shaped guides, each of said guides being associated with one of said pairs of said rollers, said circular inner surfaces of each of said ring-shaped guides engaging the outer surfaces of the respective associated pair of rollers whereby said electromagnet moves progressively along the surface of the object under inspection at a set distance therefrom when said guides rotate.

2. A magnetizing device for recording flaw fields in the process of magnetographic inspection, comprising: a two-pole electromagnet having a working pole surface intended for contacting the surface of an object under inspection; four rollers rotatably mounted in pairs on each of the two poles of said electromagnet, each having a rotation axle defining a rotation axis, the rotation axes of said rollers all being arranged in one plane parallel to said working pole surface of said electromagnet; two ring-shaped guides each having a circular inner surface and each having a circular outer surface for rolling along the object under test, said ring-shaped guides being rigidly secured together in parallel relation to each other by a bar for simultaneous rotation of said ringshaped guides, each of said guides being associated with one of said pairs of said rollers, said circular inner surfaces of each of said ring-shaped guides engaging the outer surfaces of the respective associated pair of rollers whereby said electromagnet moves progressively along the surface of the object under inspection at a set distance therefrom when said guides rotate, wherein a ring gear is provided on said inner surfaces of said guides in said outer surfaces of said rollers in order to form gear engagement between said guides and said rollers, which prevents slipping of said rollers relative to said guides.

3. A magnetizing device for recording flaw fields in the process of magnetographic inspection, comprising: a two-pole electromagnet having a working pole surface intended for contacting the surface of an object under inspection; four rollers rotatably mounted in pairs on each of the two poles of said electromagnet, each having a rotation axle defining a rotation axis, the rotation axes of said rollers all being arranged in one plane parallel to said working pole surface of said electromagnet; two ring-shaped guides each having a circular inner surface and each having a circular outer surface for rolling along the object under test, said ring-shaped guides being rigidly secured together in parallel relation to each other by a bar for simultaneous rotation of said ring-shaped guides, each of said guides being associated with one of said pairs of said rollers, said circular inner surfaces of each of said ring-shaped guides engaging the outer surfaces of the respective associated pair of rollers whereby said electromagnet moves progressively along the surface of the object under inspection at a set distance therefrom when said guides rotate, wherein said electromagnet is U-shaped.

4. A magnetizing device for recording flaw fields in the process of magnetographic inspection, comprising: a two-pole electromagnet having a working pole surface intended for contacting the surface of an object under inspection; four rollers arranged in pairs for mounting on each of the two poles of said electromagnet, each having a rotation axle defining a rotation axis, the rotation axes of said rollers all being arranged in one plane parallel to said working pole surface of said electromagnet; two ring-shaped guides each having a circular inner surface and each having a circular outer surface for rolling along the object under test, said ring-shaped guides being rigidly secured together in parallel relation to each other by a bar for simultaneous rotation of said ring-shaped guides, each of said guides being associated with one of said pairs of said rollers, said circular inner surfaces of each of said ring-shaped guides engaging the outer surfaces of the respective associated pair of rollers whereby said electromagnet moves progressively along the surface of the object under inspection at a set distance therefrom when said guides rotate; four half-axles, each secured on a respective one of said rollers to provide substantially uniform displacement for all rollers in relation to said rotation axles thereof and parallel thereto; four horizontal platforms rigidly secured in pairs to said poles of said electromagnet and arranged in one plane so that said electromagnet is movably mounted on said half-axles by means of said platforms; bearings mounted on said rotation axles of said rollers; a rigid frame supporting said bearings; said half-axles, horizontal platforms, rollers and rigid frame being interconnected so that said electromagnet, besides its progressive motion along said surface of the object under inspection, is arranged to move periodically in the vertical direction relative to said surface of the object under inspection and in one extreme position said electromagnet contacts with said surface of the object under inspection by said working pole surface and in the other extreme position it locates said working pole surface at a set distance from the surface of the object under inspection.

5. A magnetizing device as claimed in claim 4, wherein a ring gear is provided on said inner surfaces of said guides and said outer surfaces of said rollers in order to form gear engagement between said guides and said rollers, which prevents slipping of said rollers relative to said guides.

6. A magnetizing device as claimed in claim 4, wherein said electromagnet is U-shaped.

7. A magnetizing device as claimed in claim 4, wherein said half-axles are arranged on said rollers so that their displacement relative to said rollers rotation axles can be changed to adjust the magnitude of the set distance between said working pole surface of said electromagnet and said surface of the object under inspection.

* * * * *